United States Patent [19]

Nohda

[11] Patent Number: 4,787,743
[45] Date of Patent: Nov. 29, 1988

[54] APPARATUS FOR MEASURING THE RADIUS OF CURVATURE

[75] Inventor: Masao Nohda, Yokosuka, Japan

[73] Assignee: Sun Hig-Tech Kabushiki Kaisha, Kenagawa, Japan

[21] Appl. No.: 73,514

[22] Filed: Jul. 15, 1987

Related U.S. Application Data

[62] Division of Ser. No. 791,894, Oct. 28, 1985, Pat. No. 4,702,596.

[30] Foreign Application Priority Data

Jun. 5, 1985 [JP] Japan .................. 60-121938

[51] Int. Cl.$^4$ ............................ A61B 3/10; G01B 9/00
[52] U.S. Cl. .................................. 356/124; 351/212; 351/247
[58] Field of Search ............... 356/124, 125, 126, 127; 351/212, 247

[56] References Cited

U.S. PATENT DOCUMENTS 4,572,628  2/1986  Nohda ................. 351/212
4,588,270  5/1986  Tamaki ................ 351/212

Primary Examiner—F. L. Evans
Attorney, Agent, or Firm—Bauer & Schaffer

[57] ABSTRACT

A plurality of light sources are caused to impinge in predetermined directions onto an optical system to be inspected. The reflected beams from the optical system are received by two or more pairs of photoelectric converting elements and the radius of curvature of the above mentioned optical system is measured on the basis of the phase difference of the output signals between the photoelectric converting elements forming the respective pairs. The reflected beams are first converted into a slit shaped series of beams, the angle of inclination of each of which, to which to the scanning direction, is made in two or more different known angles. An output device emitting the discriminating signal of the angle of inclination of the beams is provided and the discriminating signal and phase difference inputted to an operating circuit to obtain a refractive power.

5 Claims, 9 Drawing Sheets

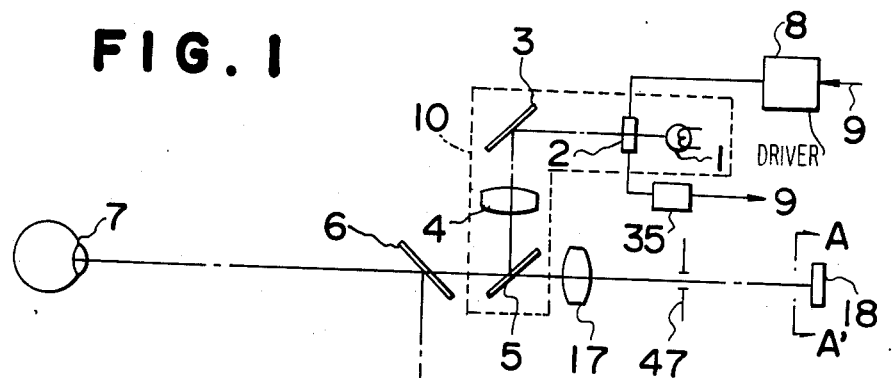
FIG. 1
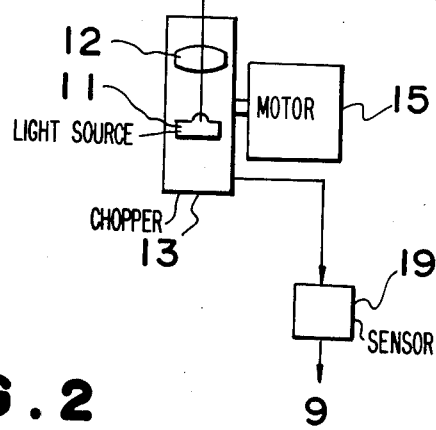
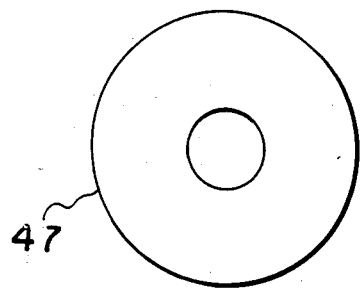
FIG. 2
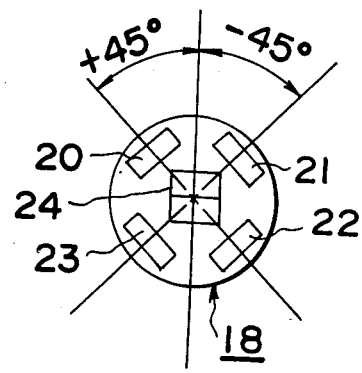
FIG. 3

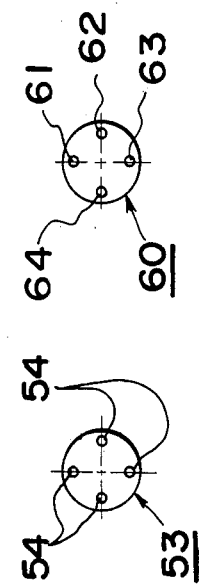
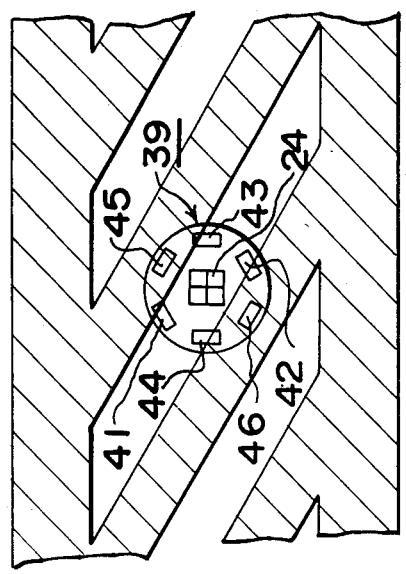
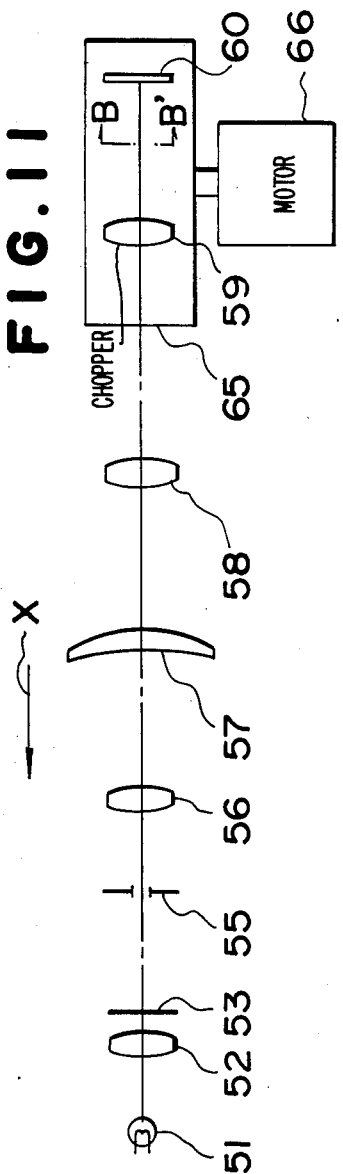

APPARATUS FOR MEASURING THE RADIUS OF CURVATURE

RELATED APPLICATION

This is a division of Ser. No. 791,894 filed Oct. 28, 1985, now U.S. Pat. No. 4,702,596 issued Oct. 27, 1987.

FIELD OF THE INVENTION

This invention relates to apparatus for measuring the radius of curvature of an optical system and particularly to apparatus which can be utilized as an eye refractometer, automatic lens meter or the like.

There are fundamentally three kinds of systems for measuring the eye's refractive power: a coinciding system, image forming system and shadow inspecting system. The present invention is the shadow inspecting system.

BACKGROUND OF THE INVENTION

The prior art shall be explained with reference to an example of an apparatus for the automatic measurement of the eye's refractive power.

In conventional automatic eye refractive power measuring apparatus, various improvements have been made to simplify the mechanism, to facilitate its production and adjustment, to reduce the measuring time and to increase the measuring precision. Thus, there is provided an automatic eye refractive power measuring apparatus shown in the Japanese Official Gazette under Laid Open Patent Application No. 160538/1980, corresponding to U.S. Pat. No. 4,353,625.

Defects, however, exist in this automatic eye refractive power measuring apparatus, in that, as an image rotating prism is required to rotate beams, it is difficult, in the manufacture and adjustment, to rotate the image rotating prism around the optical axis as a center. The amount of light will attenuate due to the reflection of the image rotating prism and the measuring time can not be significantly reduced.

Therefore, in order to eliminate such defects, an automatic eye refractive power measuring apparatus shown in the Japanese Official Gazette under Laid Open patent application No. 165735/1982 corresponding to U.S. Pat. No. 4 526,451 has been provided.

In this latter apparatus, the eye to be inspected is periodically scanned alternatively in two known directions using slit-shaped illuminating beams at the same angle of inclination to the scanning direction. The reflected light from the two beams is received by two pairs of photoelectric converting elements and the phase difference of output signals between the photoelectric converting elements forming the respective pairs is employed to measure the refractive power of the inspected eye.

For a shadow projecting device, in order to make slit-shaped illuminating beams scan alternatively in two known directions, a light source, a prism and a rotary copper is provided as seen in FIGS. 16 and 17. The rotary chopper 113 is provided with slit apertures 114 all formed at the same angle of inclination to the rotating direction X, FIG. 16 is a developed view of the rotary chopper 113.

If it is assumed that there is no astigmatism in the eye to be inspected, and as in FIG. 17(a) the slit-shaped illuminating beams are made to scan the eye in one direction or as in FIG. 17(b) the slit-shaped illuminating beams are made to scan in the other direction, the light reflected from the eye of each of the slit-shaped illuminating beams will run respectively in the direction indicated by the arrow V or W through two pairs of photoelectric converting elements 120, 122 and 121, 123 onto the light receiving surface of a photoelectric converter 136.

If it is assumed that there is an astigmatism in the eye being inspected, the above mentioned reflected lights will deviate by an angle (which shall be hereinafter called a column axis angle) corresponding to the direction of the main warp line of the astigmatism as compared with the direction shown on FIGS. 17(a) and 17(b).

Therefore, if S represents a spherical refractive power and C represents a columnar refractive power, and the slit-shaped illuminating beams are made to scan in the direction corresponding to FIG. 17(a), the value $D_1$ obtained from the phase difference of the output signals of the photoelectric converting elements 120 and 122 will be $$D_1 = S + C \cos^2 \theta \tag{1}$$

and the value $D_2$ obtained from the phase difference of the output signals of the photoelectric converting elements 121 and 123 will be $$D_2 = \frac{C}{2} \sin 2\theta \tag{2}$$

When, however, slit-shaped illuminating beams are made to scan in the direction corresponding to FIG. 17(b), the value $D_3$ obtained from the phase difference of the output signals of the photoelectric converting elements 120 and 122 will be $$D_3 = -\frac{C}{2} \sin 2\theta \tag{3}$$

and the value $D_4$ obtained from the phase difference of the output signals of the photoelectric converting elements 121 and 123 will be $$D_4 = S + C \sin^2 \theta \tag{4}$$

Therefore, from the above formulae (1) to (4), the spherical refractive power S, columnar refractive power C and column axis angle $\theta$, that is, the refractive power can be determined.

However, in the automatic eye refractive power measuring apparatus shown in the above mentioned application, Japanese Publication No. 165735/1982, the slit-shaped illuminating beams must be made to scan alternatively to two known directions. Therefore, instead of using an image rotating prism, a prism which is not required in the Japanese Publication No. 160538/1980 is required. Consequently the effectiveness to the amount of light is not so high, and two light sources are required instead of the one light source required in the Japanese Publication No. 160538/1980—thus, a new defect in the manufacture is created in that the beams and light of the two light sources must be made to coincide respectively with each other.

Incidentally, as the eye is also an optical system, it is apparent that the above described argument is not limited to apparatus for the automatic measuring of eye refractive power but can be also used in such other refractive power measuring optical systems as a lens meter and a radius of curvature measuring apparatus.

That is to say, the same defect as is described above is produced also, for example, in a lense meter such as described in Japanese Laid Open Patent application No. 168137/1982 to which the above mentioned Japanese Application No. 165735/1982 is applied and a radius of curvature radius measuring apparatus (such as in Japanese Laid Open Patent Application No. 197405/1982).

BRIEF SUMMARY OF THE INVENTION

The present invention has it as an object the provision of an eye-refractometer which is easy to manufacture, reduces measuring time and is capable of a high precision.

Therefore, according to the present invention, apparatus wherein the optical system, to be inspected, is scanned with slit-shaped illuniating beams. The reflection of the beams from the optical system are received with two or more pairs of photoelectric converting elements and the refractive power is measured on the basis of the phase difference of the output signals between the photoelectric converting elements forming the respective pairs. The angle of inclination of the slit-shaped illuminating beams to the scanning direction is made two or more different known angles. An output device is provided supplying the discriminating signal of the angle of inclination which together with the phase difference are supplied to an operating circuit to obtain a refractive power.

According to the present invention, since the angle of inclination of the slit-shaped illuminating beams to the scanning direction of the inspected optical system has two or more different known angles, then simply scanning the optical system in only one direction, with the slit-shaped illuminating beams, will be substantially equivalent to alternatively scanning the optical system in the two known directions with slit-shaped illuminating beams all at the same angle of inclination to the scanning direction.

Therefore, according to the present invention, it is not necessary to make the slit-shaped illuminating beams scan alternatively in two known directions, no prism is required and only one light source will do. Further it is not necessary to use an image rotating prism. Therefore, the manufacture is easy, the measuring time is reduced and a high precision measurement is possible.

BRIEF DESCRIPTION OF THE DRAWINGS

FIG. 1 is a schematic view of an optical system, showing an embodiment of the present invention;

FIG. 2 is a plan view of a diaphragm used in the apparatus of FIG. 1;

FIG. 3 is a view of the apparatus as seen in the direction indicated by arrows A—A' in FIG. 1;

FIG. 11 is a schematic view of an optical system, showing another embodiment of the present invention;

FIG. 12 is a plan view of a diaphragm employed in the embodiment of FIG. 11;

FIG. 13 is a view taken in the direction of arrows B-B' in FIG. 11;

DETAILED DESCRIPTION OF THE INVENTION

Figure 4:
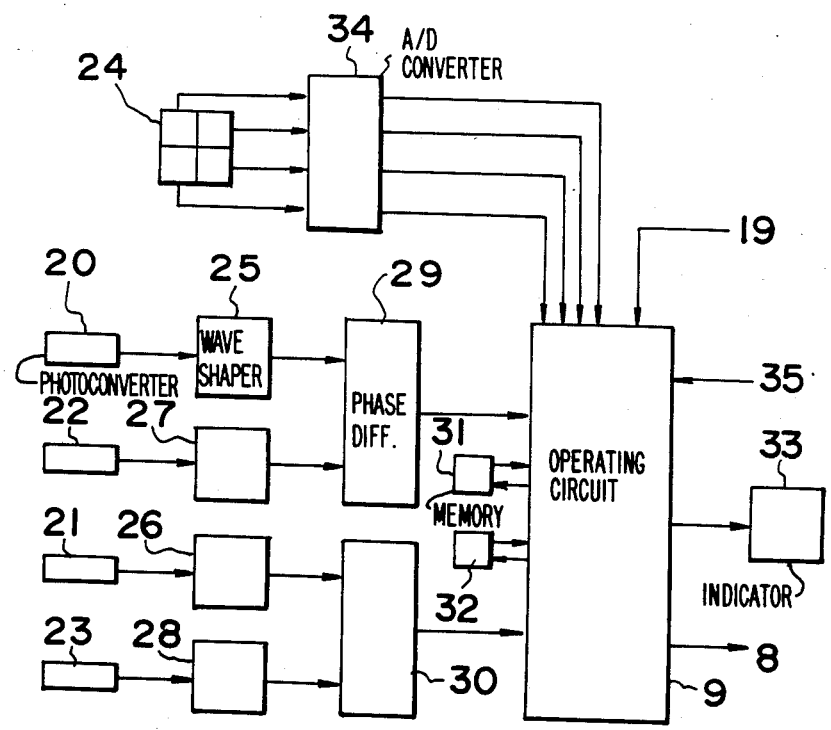
FIG. 4 is a circuit diagram for the apparatus of FIG. 1.

The present invention shall be described in detail with reference to an automatic eye refractive power measuring apparatus. As seen in FIG. 1, a light source 1 illuminates a visual target 2, from which are reflected, by a reflector 3, and made substantially parallel by a collimator lens 4. The parallel beams are split by a first light path divider 5, to pass in part through a second light path divider 6 so as to impinge on the eye 7 being inspected, which is fixedly sighted on the visual target 2. Here, the visual target 2 is movable in the direction of the optical axis by a driving means 8, which as will be described later, is controlled by the output of an operating circuit 9 (FIG. 4) so that the visual target 2 may be movable to a position in which the eye 7 can become fixedly sighted on the visual target, without adjustment, forming a so-called automatic fog device. Collectively the light source 1, visual target 2, reflector 3, collimator lens 4 and the first light path divider 5 form a visual target optical system 10 which enables the eye 7 to fixedly sight the visual target 2 during the measurement and reduces the instrument myopia of the eye caused during the measurement.

Figure 5:
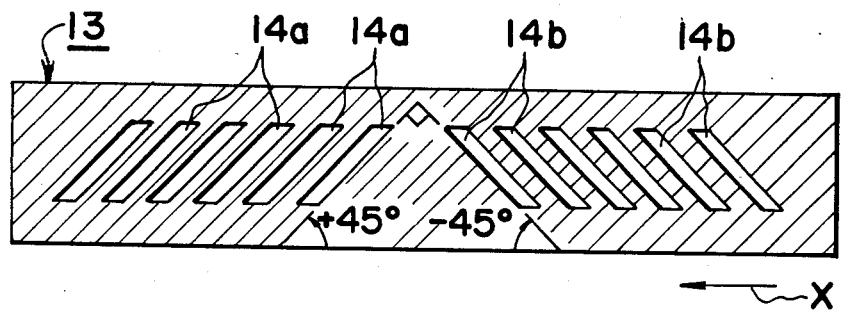
FIG. 5 is a developed view of a rotary light beam chopper for the apparatus of FIG. 1.

Further, a second light source 11 such as, an infrared LED (light emitting diode), and a condenser lens 12 form an image of the second light source 11 on the cornea of the eye 7 being inspected. The light passes through a rotary chopper 13 provided as seen in FIG. 5 with slit-shaped apertures 14$a$ and 14$b$, the rotary chopper being rotated at a fixed velocity in a fixed direction by a motor 15.

Therefore, the beams emitted from the light source 11 passing through the condenser lens 12, is chopped by the rotary chopper 13 into slit-shaped illuminating beams. The slit-shaped beams are reflected by the second light path divider 6, being condensed on the cornea of the eye 7 and projected on the fundus of the eye. That is to say, the slit-shaped illuminating beams scan the eye 7 in one direction.

Further, the photoelectric converter 18, a lens 17 for conjugating this photoelectric converter 18 and the cornea of the eye 7 with each other and a diaphragm 47 having a circular aperture with the optical axis as a center is provided. The shape of the diaphragm as seen in the optical axis direction is shown in FIG. 2).

Therefore, the slit-shaped illuminating beams projected on to the bottom of the eye 7 are reflected by the eye bottom and pass through the first light path divider 5 and second light path divider 6, being condensed by the lens 17 to pass further through the diaphragm 47 and illuminate the light receiving surface of the photoelectric converter 18.

According to the present invention, the angle of inclination of the slit-shaped illuminating beams to the scanning direction of the eye 7 is made in two or more different known angles.

In the case of the embodiment illustrated, in FIG. 5 showing the developed view of the rotary chopper 13, the angle of inclination of the first slit-shaped apertures 14a to the rotating direction X of the rotary chopper 13 is +45 degrees, while the angle of the inclination of the second slit-shaped apertures 14b is −45 degrees.

Further, in the present invention, an output means 19 is provided emitting a discriminating signal showing at what angle of inclination the slit-shaped illuminating beams scan the eye 7. This output means 19 is, for example, a sensor detecting the angle of rotation of the rotary chopper 13 corresponding to the position of the slit-shaped aperture 14a or 14b.

As seen in FIG. 3, there is provided on the light receiving surface of the photoelectric converter 18, four photoelectric converting elements 20, 21, 22 and 23 arranged outside the optical axis and a four-part photoelectric converting element 24 having as its center of division the optical axis as already known (See Japanese Patent application No. 165735/1982).

One pair of photoelectric converting elements 20 and 22 are arranged symmetrically with and diametrically opposite to each other with respect to the optical axis in one measuring warp line direction, that is, on the line inclined +45 degress to the line intersecting rectangularly with the optical axis within the paper surface of FIG. 1 and the second pair of photoelectric converting elements 21 and 23 are arranged symmetrically with and diameterically opposed to each other with respect to the optical axis in the measuring warp line direction intersecting rectangularly with the above mentioned warp line direction, that is, one the line inclined at −45 degress with the line intersecting rectangularly with the optical axis within the paper surface of FIG. 1.

The four-part photoelectric converting element 24 receives the reflected light from the eye 7 for alignment. When the eye 7 and the measuring apparatus are well aligned with each other, the reflected image will be equally incident upon the respective elements of the four-part photoelectric converting element 24 and the output of each of the respective element parts will be equal. However, when the eye 7 and the measuring apparatus are not well aligned, the output of each of the respective elements will not be equal and the direction of the deviation can be determined from the relative size of the outputs.

As shown in FIG. 4, the photoelectric converting elements 20, 21, 22 and 23 are connected respectively to waveform shaping circuits 25, 26, 27, and 28. One pair of waveform shaping circuits 25 and 27 shape the waveforms of the output signals of the first pair of photoelectric converting elements 20 and 22 and are connected to a first phase difference measuring circuit 29. The second pair of waveform shaping circuits 26 and 28 shape the waveforms of the output signals of the second pair of photoelectric converting elements 21 and 23 and are connected to a second phase difference measuring circuit 30. The first phase difference measuring circuit 29 and the second phase difference measuring circuit 30 are connected to the operating circuit 9 to which is further connected the discriminating signal from output means 19. The operating circuit 9 is provided with memory circuits 31 and 32 which store the outputs of the first phase difference measuring circuit 29 and second phase difference measuring circuit 30 when the slit-shaped illuminating beams derived from the first slit-shaped apertures 14a scan the eye 7 and the outputs of the first phase difference measuring circuit 29 and second phase difference measuring circuit 30 when the slit-shaped illuminating beams derived from the second slit-shaped apertures 14b scan the eye 7. The operating circuit 9 then operates as described later utilizing the memorized values to compute the column axis angle $\theta$, spherical refractive power S and columnar refractive power C and indicates the results in an indicating device 33.

On the other hand, the outputs of the respective elements of the four-part photoelectric converting element 24 are converted to digital signals by an A-D converter 34 and are then entered into the operating circuit 9. The operating circuit 9 compares the sizes of the signals from the respective four-part element 24 with a maximum value and emits into the indicating device 33 a signal indicating the direction intersecting rectangularly with the optical axis and the movement in the optical axis direction for alignment. The operating circuit 9 further is provided with the output of a position detecting means 35 sensing the position on the optical axis of the visual target 2 and emits a signal to the driving means 8 so as to increment all move the visual target 2 by a fixed step in a direction to reduce the operated spherical refractive power S and columnar refractive power C. That is to say, such automatic fogging device as is disclosed in U.S. Pat. No. 4,190,332 is formed of the visual target 2, position detecting means 35, operating circuit 9 and driving means 8.

The operation of the aforementioned embodiment of present invention as an automatic eye refractive power measuring apparatus shall be explained in the following.

The inspector aligns the eye 7 which is being inspected, with the measuring apparatus, while observing the indicating means 33. After the completion of the alignment, measuring switch is switched on and the automatic measurement began.

When the slit-shaped illuminating beams derived from the first slit-shaped apertures 14a scan they eye 7, the operating circuit 9 will discriminate the conditions and will memorize in the memory circuit 31 the phase difference (the average value of many measurements being generally used) obtained from the phase difference measuring circuits 29 and 30. Further, when the slit-shaped illuminating beams derived from the second slit-shaped apertures 14b scan the eye 7, the operating circuit 9 will discriminate the condition and will memorize in the memory circuit 32 the phase difference obtained from the phase difference measuring circuits 29 and 30. When the above mentioned memorization is completed, the operating circuit 9 will read the memories from the memory circuits 31 and 32 and will compute the refractive power, that is, the columnar axis angle $\theta$, spherical refractive power S and columnar refractive power C of the eye being inspected. Then, the operating circuit 9 will provide a signal to the driving means 8 to move the visual target 2 in the direction of relaxing the eye 7 as a result of this computed refractive power, that is to say, the automatic fogging means will operate on the basis of the computed refractive power. The operation is repeated, for each step until the spherical refractive power S no longer varies, even if the visual target 2 is further varied. The operating circuit 9 will then indicate this final refractive power S in the indicating means 33.

The reason why the refractive power can be determined by the operation of the operating circuit shall be described in the following.

Figure 6A:
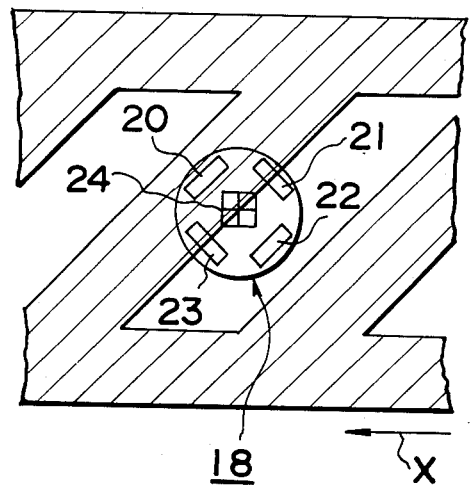
FIGS. 6($a$) and 6($b$) are explanatory views showing scanning employing the reflected lights of the slit-shaped beams.
Figure 6B:
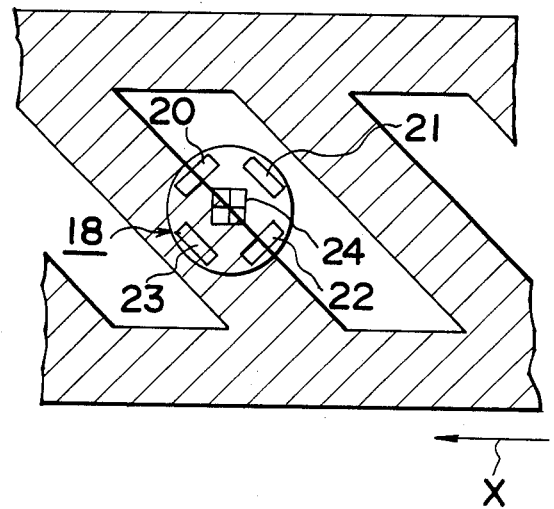
Figure 17A:
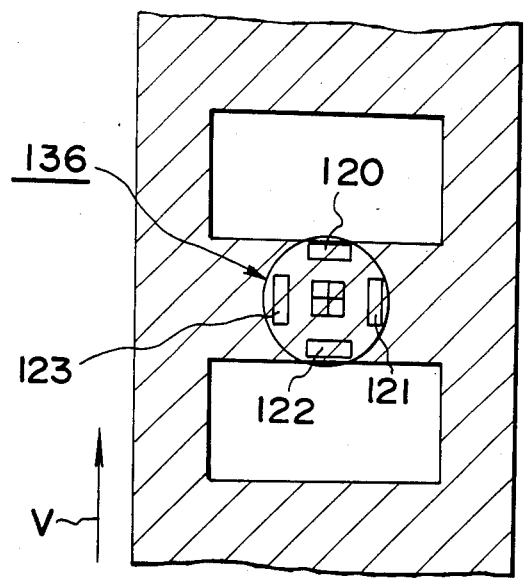
FIGS. 17($a$) and 17($b$) are views similar to FIGS. 6($a$) and 6($b$) showing a prior art apparatus.
Figure 17B:
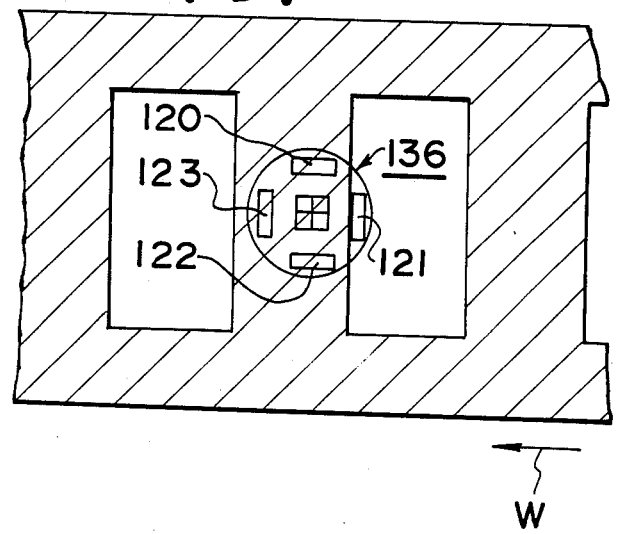

If there is no astigmatism in the eye 7 being inspected, when the slit-shaped illuminating beams based on the first slit-shaped apertures 14a scan the eye 7 and the reflected light will impinge on the light receiving surface of the photoelectric converter 18 in the direction indicated by the arrow X in FIG. 6(a). When, however, the slit-shaped illuminating beams based on the second slit-shaped apertures 14b scan the eye 7, the reflected light will run in the direction indicated by the arrow X in FIG. 6(b). The condition of FIG. 6(a) will be substantially identical with the condition shown in FIG. 17(a) and the condition of FIG. 6(b) will be substantially identical with the condition shown in FIG. 17(b) as explained hereinbefore the background of the invention.

Therefore, when the slit-shaped illuminating beams derived from the first slit-shaped apertures 14a scan the eye 7 being inspected, the value obtained from the phase difference of the output signals of the photoelectric converting elements 20 and 22 is represented by $D_1'$ and the value obtained from the phase difference of the output signals of the photoelectric converting elements 21 and 23 is represented by $D_2'$. When the slit-shaped illuminating beams dervided from the second slit-shaped apertures 14b scan the eye 7, the value obtained from the phase difference of the output signals of the photoelectric converting elements 20 and 22 is represented by $D_3'$ and the value obtained from the phase difference of the output signals of the photoelectric converting elements 21 and 23 is represented by $D_4'$. Thus:

$$D_1' = S + C \cos^2 \theta \quad (5)$$

$$D_2' = \frac{C}{2} \sin 2\theta \quad (6)$$

$$D_3' = -\frac{C}{2} \sin 2\theta \quad (7)$$

$$D_4' = S + C \sin^2 \theta \quad (8)$$

Therefore, as the unknown factors are C, S and $\theta$ and there are three measured data of $D_1'$, $D_2'$, $(= -D_3')$ and $D_4'$. Therefore by loading these equations (5), (6) (or (7)) and (8) into the operating circuit 9, the column axis angle $\theta$, spherical refractive power S and columnar refractive power C can be computed.

However, if such operation as is described above is made by the operating circuit 9, it will take time for the computation of the constants between the outputs of the phase difference measuring circuits 29 and 30 and the values $D_1'$, $D_2'$, $D_3'$ and $D_4'$ will vary depending on the arrangement of the optical system. Therefore, in actual practice the apparatus is calibrated by using an imitation eye of known refractive power and the outputs of the phase difference measuring circuits 29 and 30 are memorized by the operating circuit 9 as corresponding to the above described known refractive power to eliminate the above described disadvantages. As there are three unknown factors, C, S and $\theta$ and three measured data values (actually there are four values but two of them have axes intersecting rectangularly with each other and are different only in sign and therefore these are effectively only three values, the refractive power (determined by C, S and $\theta$) can be directly determined.

If the outputs of the phase difference measuring circuits 29 and 30 are made to correspond to the refractive power, the optical system will be able to be comparatively freely arranged without any complications.

Therefore, for example, the diaphragm 47 will be able to be moved to any position on the measuring optical axis.

Figure 7A:
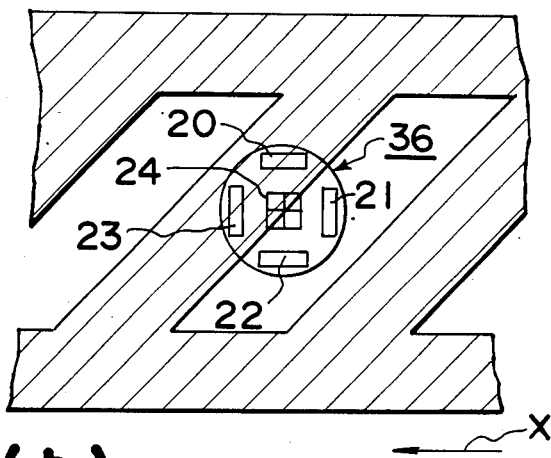
FIGS. 7($a$) and 7($b$) are views similar to those of FIGS. 6($a$) and 6($b$) showing another embodiment.
Figure 7B:
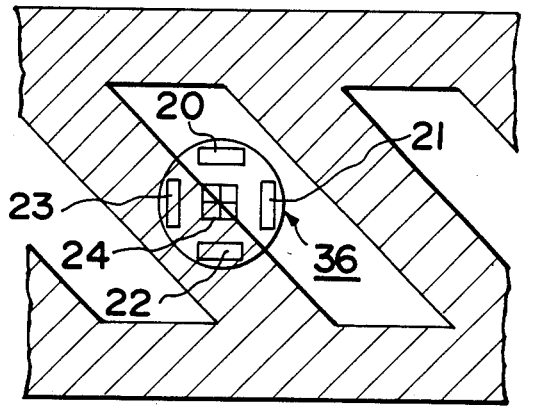

Further, if the direction of each pair of photoelectric converting elements is known, it is not required that they intersect rectangularly and they can be located as desired. For example, as seen in FIG. 7a and 7b, a photoelectric converter 36 in which the arrangement of the photoelectric converting elements 20, 21, 22 and 23 such as those used in the photoelectric converter 18 are rotated by 45 degrees, may be used instead. Compare this with FIGS. 6(a) and 6(b), FIGS. 7(a) and 7(b).

Figure 8:
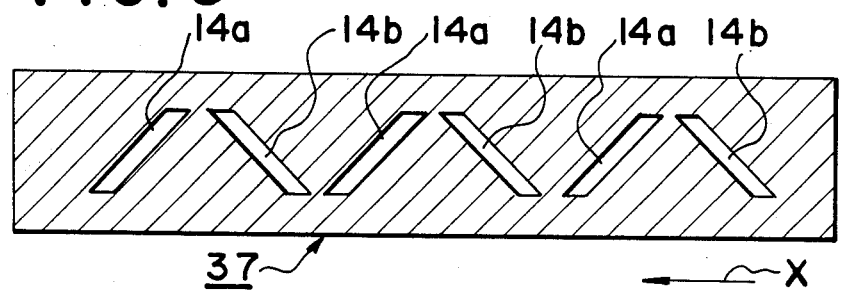
FIG. 8 is a view similar to FIG. 5 showing another embodiment of a rotary chopper.

Further, as the angle of inclination of the slit-shaped illuminating beams scanning the eye may be made in two or more different angles, the slit-shaped apertures may be freely arranged. For example, a rotary chopper 37 may be used in which the arrangements of the first slit-shaped apertures 14a and second slit-shaped apertures 14b are modified as shown in FIG. 8.

It is also not required that the two or more different known angles, of inclination of the slit-shaped apertures be limited to 45 degrees or the like but they can be freely selected. Also, the angle of inclination of the slit-shaped apertures need not be limited to two different known angles but may in fact be three or more different known angles. Also, the photoelectric converting elements need not be limited to two pairs but may be three or more pairs.

Figure 9:
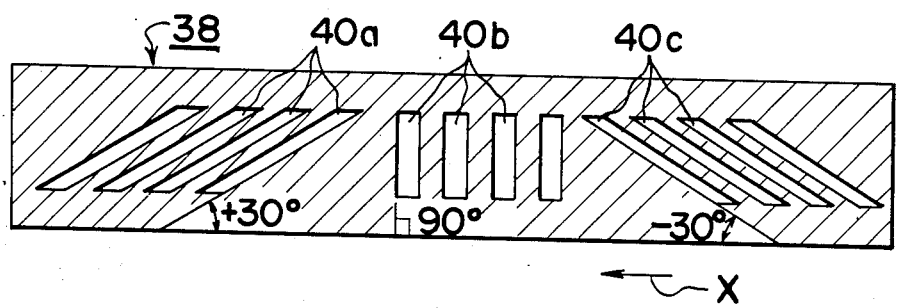
FIG. 9 is a view similar to FIG. 5 showing still another embodiment of a rotary chopper.
Figure 10:
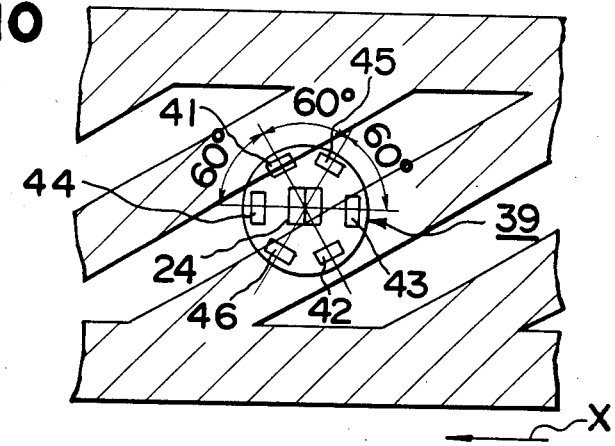
FIGS. 10($a$), 10($b$) and 10($c$) are views similar to FIG. 5 showing still further embodiments of rotary choppers.
Figure 10:
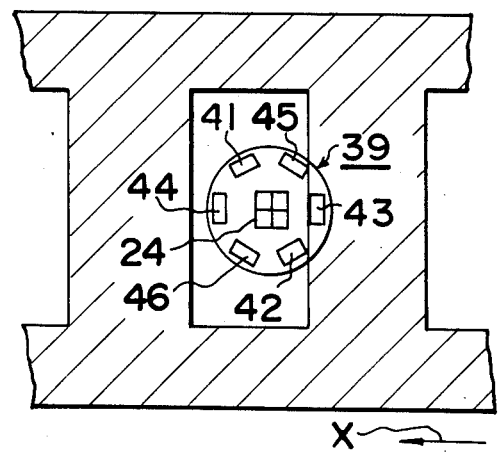

For example, a rotary chopper 38 such as shown in FIG. 9 may be used instead of the rotary chopper 13, and a photoelectric converter 39 as shown in FIGS. 10(a), 10(b) and 10(c) may be used instead of the photoelectric converter 18 or 36. FIG. 9 shows in its developed view the rotary chopper 38 in which the angle of inclination of the first slit-shaped apertures 40a to the rotating direction X is made +30 degrees, the angle of inclination of the second slit-shaped apertures 40b is made +90 degrees and the angle of inclination of the third slit-shaped apertures 40c is made −30 degrees.

In FIGS. 10(a) and 10(b) a photoelectric converter 39 is shown having respective pairs of photoelectric converting elements 41 and 42, 43 and 44 and 45 and 46 arranged symmetrically with respect to the optical axis on three lines respectively intersecting rectangularly with the optical axis, sixty (60) degrees with one another.

With this arrangement, if there is no astigmatism in the eye being inspected, then: when the slit-shaped illuminating beams derived from the first slit-shaped apertures 40a scan the eye 7, the reflected light will impinge on the light receiving surface of the photoelectric converter 39 in the direction indicated by the arrow X as in FIG. 10(a); when the slit-shaped illuminating beams derived from the second slit-shaped apertures 40b scan the eye 7, the reflected light will imping on the light receiving surface of the photoelectric converter 39 in the direction indicated by the arrow X as in FIG. 10(b); when the slit-shaped apertures 40c scan the eye 7, the reflected light will impinge on the light receiving surface of the photoelectric converter 39 in the direction indicated by the arrow X as in FIG. 10(c).

Consequently, if the value obtained from the phase difference of the output signals of the photoelectric converting elements 41 and 42 is represented by $D_1''$; if the value obtained from the phase difference of the output signals of the photoelectric converters 43 and 44 is represented by $D_2''$ and, if the value obtained from the phase difference of the output signals of the photoelectric converters 45 and 46 is represented by $D_3''$, then:

$$D_1'' = S + C \cos^2(\theta - 60) \quad (9)$$

$$D_2'' = S + C \cos^2 \theta \quad (10)$$

$$D_3'' = S + C \cos^2(\theta + 60) \quad (11)$$

Therefore, the operating circuit 9 can be set up to compute the unknown factors C, S and $\theta$ from the three measured data values $D_1''$, $D_2''$ and $D_3''$, using the above equations (9), (10) and (11). Consequently the column axis angle $\theta$, spherical refractive power S and columnar refractive power C can be determined.

In this case, a waveform shaping circuit and phase difference measuring circuit will be provided.

In the above explanation, the shapes of the slit-shaped apertures shown in FIGS. 5, 8 and 9 have been explained by using the developed views of the rotary choppers. When the chopper is actually cylindrical, the slit-shaped apertures will preferably have a fixed angle of inclination.

However, the above described apparatus for measuring the eye refractive power can be used also as a lens meter without any modification in principle. In the case of measuring the eye refractive power, it is a feature in the formation that, in order to measure the reflected beams in the eye bottom, the illuminating beams pass twice through the inspected optical system (the crystalline lens of the inspected eye 7) and the projecting light path and measuring light path are used partly in common. However, in the case of a lens meter, the lens to be inspected can usually be measured by one pass and the projecting light path and measuring light paths are formed on the opposite sides of the inspected lens. Needless to say, if the beams passing through the inspected lens are again made incident upon the inspected lens by a reflector, the arrangement can be made the same as of the above described eye refractive power measuring apparatus.

An embodiment making the present invention a lens meter shall be briefly explained in relation to FIG. 11 as follows. By the way, this embodiment relates to an improvement of the lens meter shown in the Japanese Laid Open Patent application No. 168137/1982.

A light source 51, a condenser lens 52, a diaphragm 53 having four apertures 54 are provided. As seen in FIG. 12 the apertures 54 are arranged in a circle concentric with the optical axis in dianetically opposed pairs, second diaphragm 55 similar to the diaphragm 47 shown in FIG. 1, a collimator lens 56 are also provided, and the diaphragm 55 is preferably substantially at the focus of the collimator lens 56. The reference numeral 57 represents a lens to be inspected. The four apertures 54 of the diaphragm 53 form images on the inside surface of the lens 57. Second and third collimator lenses 58 and 59 and a photoelectric converter 60 complete the optical arrangement. As shown in FIG. 13, the photoelectric converter 60 is provided with converting elements 61, 62, 63 and 64 arranged in opposing pairs aa-long a circle concentric with the optical axis. The axes of the converting elements 61, 62, 63, and 64 coincide respectively with the axes of the four apertures 54 of the diaphragm 53. Also, the photoelectric converter 60 must be substantially conjugated with the inside surface of the inspected lens 57. A rotary chopper 65 and a motor 66 for rotating the rotary chopper 65 are arranged along the optical axis.

In the optical system arranged as in the above, the beams emitted from the light source 51 will pass through the condenser lens 52, diaphragms 53 and 55 and collimator lens 56, being refracted by the inspected lens 57, and chopped by the rotary chopper 65, passing subsequently through the collimator lens 59 to reach the photoelectric converter 60. Therefore, phase differences proportional to the refractive power of the inspected lens 57 will be produced respectively between the output signals of the photoelectric converting elements 61 and 63 and between the output signals of the photoelectric converting elements 62 and 64 of the photoelectric converter 60.

Here, if the shape of the rotary chopper 65 is made the same as of the rotary chopper 13 shown in FIG. 5 or even the rotary chopper 38 shown in FIG. 9, the refractive power of the inspected lens 57 will be able to be determined by the formulae (5) to (8) or formulae (9) to (11) respectively.

By the way, it is needless to say that the operating circuit and other components are used in the same manner in this embodiment as in the aforementioned automatic eye refractive power measuring apparatus.

Further, the embodiment of the present invention is apparatus for measuring the radius of curvature be explained in the following. By the way, this embodiment is an improvement of the apparatus shown in Japanese Laid Open Patent application No. 197405/1982.

Figure 14:
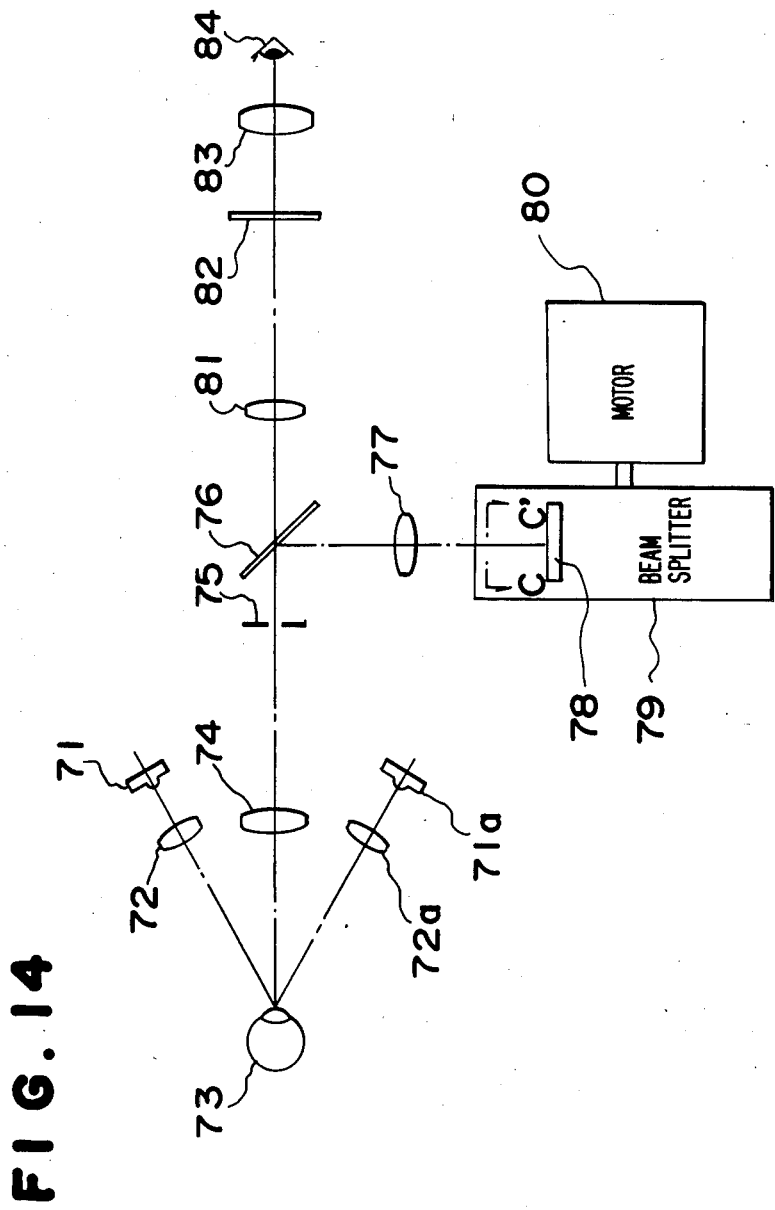
FIG. 14 is a schematic view of an optical system, showing a third embodiment of the present invention.
Figure 15:
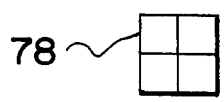
FIG. 15 is a view taken in the direction of arrows C-C' in FIG. 14.
Figure 16:
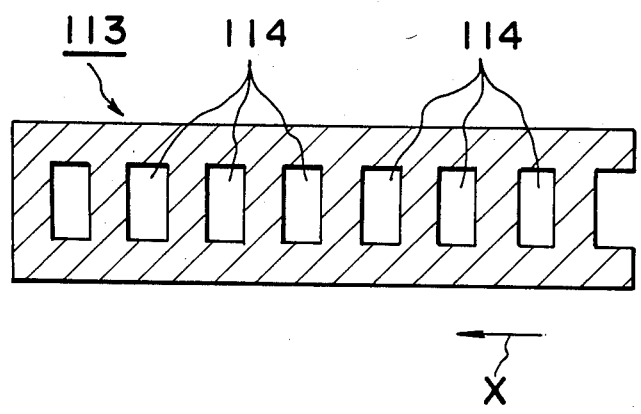
FIG. 16 is a view similar to FIG. 5 showing the prior art rotary chopper.

Light sources 71 and 71a and collimator lenses 72 and 72a are provided together with another pair of light sources and another pair of collimator lenses (not illustrated) but located in a direction vertical to the paper surface of FIG. 14. These two pairs of beams correspond to the four apertures 54 of the diaphragm 53 shown in FIG. 11. Along the optical axis of the eye 74 to be inspected is a collimator lens 74, the focus of the collimator lens 74 being substantially coincided with the cornea of the eye 73. A diaphragm 75 which is located preferably at the opposite focus of the collimator lens 74. Reference numeral 76 represents a beam splitter; 77, 78, 79 and 80 are elements of a measuring optical system; 81, 82, 83 and 84 are elements of a positioning optical system. Elements 77 and 81 all collimator lenses by which images projected on the cornea of the inspected eye 73 are formed on elements 78 and 82 which are the photoelectric converter and reticle respectively. It is preferable that the foci of both collimator lenses 77 and 81 substantially coincide with the diaphragm 75. A rotary chopper 79 and a motor 80 for rotating the chopper is provided. A four-part element of the type shown in FIG. 15 is employed as the photoelectric converter 78. By the way, such four-part element as is shown in FIG. 15 may be used also for the photoelectric converter 60 in the optical system of the lens meter shown in FIG. 11. The reference numeral 83 represents an eyepiece of the inspector's eye 84.

In the optical system arranged as in the above, two pairs or four beams are emitted from the light sources 71 and 71a and the light sources intersecting rectangularly (perpendicularly) with these light sources will be reflected by the cornea of the inspected eye 73, passing through the collimator lens 74 the diaphragm 75 and will be split by the beam splitter 76.

One of the split beams will pass through the collimator lens 81, passing further through the reticle 82, the eyepiece 83 and will be observed by the inspector's eye 84. Here, the inspector will focus and center the four beams projected on the cornea of the inspected eye 73.

The other of the split beams will pass through the collimator lens 77 to the photoelectric converter 78. Phase differences proportional to the respective radii of curvature will be produced between the output signals of the respective pairs of the four-part element of the photoelectric converter 78.

Here, if the shape of the rotary chopper 79 is made the same as of the rotary chopper 13 shown in FIG. 5 or the rotary chpper 38 shown in FIG. 9, the radius of curvature of the inspected eye 73 will be able to be determined by the formulae (5) to (8) or formulae (9) to (11).

The operating circuit and other components described earlier can be used in similar manner here as in the apparatus for automatically measuring the eye refractive power.

Also, it is apparent that, if a lens is arranged instead of the inspected eye 73, the radius of curvature of the lens will be able to be determined.

As detailed in the above, according to the present invention, the conventionally required prism is no longer required, only one light source may be used, no image rotating prism is required and therefore effects are obtained making manufacture easy, reducing the measuring time and enabling the measurement of the refractive power and radius of curvature of the inspected optical system at a high level of precision.

I claim:

1. An apparatus for measuring the radius of curvature of an optical system, having a plurality of sources of light adapted to impinge light from different directions on the optical system under investigation, said light being reflected from said optical system along the optical axis thereof, and operational means for determining the radius of curvature comprising at least two pairs of photoelectric converting elements, means for converting said reflected light into a sequence of light beams each light beam being elongated in cross section and being scanned across said photoelectric converting element in a single direction, said sequence of light beams being arranged in at least two groups with the elongated cross sections of light beams of said groups inclined in at least two different angles of inclination relative to the direction of scanning and wherein said operational means includes means for comparing the output signals received from each pair of converting elements to identify the angle of inclination of the respective light beams scanning said optical system and employing said identification in determining the radius of curvature.

2. The apparatus as claimed in claim 1, wherein said means for converting are so arranged so as to define light beams whose elongated cross sections are inclined at +45 degrees and −45 degrees to the optical axis.

3. The apparatus as claimed in claim 1, wherein said means for converting are so arranged as to define light beams inclined at +30 degrees, +90 degrees and −30 degrees to said direction of the optical axis.

4. A method for measuring the radius of curvature of an optical system comprising the steps of impinging light on the optical system to be inspected from a plurality of light sources reflecting the beams from the optical system to scan across two or more pairs of photoelectric converting elements and the radius of curvature of the above mentioned optical system is measured on the basis of the phase difference of the output signals between the photoelectric converting elements comprising converting said reflected light beam into a series of slit-shaped illuminating beams, inclining said slit-shaped illuminating beams to the scanning direction at two or more different angles of inclination, said photoelectric converting elements emitting an output discriminating signal corresponding to the angle of inclination of said mentioned slit-shaped illuminating beams scanning the photoelectric converting elements and comparing the phase difference of said discriminating signals to obtain a radius of curvature.

5. The method of measuring the radius of curvature of an optical system according to claim 4, wherein the angles of inclination of the slit-shaped illuminating beams are inclined to the scanning direction of at +30 degrees, +90 degrees and −30 degrees.

* * * * *